United States Patent
Yang et al.

(10) Patent No.: US 7,364,543 B2
(45) Date of Patent: Apr. 29, 2008

(54) PAIRED ANGLED ROTATION SCANNING PROBES AND METHODS OF USE

(75) Inventors: Changhuei Yang, Pasadena, CA (US); Jigang Wu, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 9 days.

(21) Appl. No.: 11/535,427

(22) Filed: Sep. 26, 2006

(65) Prior Publication Data

US 2007/0066871 A1 Mar. 22, 2007

Related U.S. Application Data

(63) Continuation-in-part of application No. 11/087,396, filed on Mar. 22, 2005, now Pat. No. 7,261,687.

(60) Provisional application No. 60/737,603, filed on Nov. 17, 2005, provisional application No. 60/720,936, filed on Sep. 27, 2005, provisional application No. 60/720,934, filed on Sep. 27, 2005, provisional application No. 60/770,936, filed on Sep. 27, 2005, provisional application No. 60/555,628, filed on Mar. 23, 2004.

(51) Int. Cl.
*A61B 1/07* (2006.01)
*G01J 3/45* (2006.01)

(52) U.S. Cl. .............. 600/173; 600/182; 600/176; 600/478; 356/455; 359/665

(58) Field of Classification Search ........... 600/172, 600/173, 176, 137, 182, 473, 476, 478; 385/116, 385/117; 359/837, 228, 665; 356/455
See application file for complete search history.

(56) References Cited

U.S. PATENT DOCUMENTS

| | | | |
|---|---|---|---|
| 3,229,577 A | 1/1966 | Ellinger | |
| 4,717,823 A | 1/1988 | Steimel et al. | |
| 4,824,205 A | 4/1989 | Yamashita et al. | |
| 5,133,035 A | 7/1992 | Hicks | |
| 5,425,123 A | 6/1995 | Hicks | |
| 5,732,168 A * | 3/1998 | Donald | 385/16 |
| 5,862,001 A * | 1/1999 | Sigler | 359/832 |

(Continued)

*Primary Examiner*—John P. Leubecker
(74) *Attorney, Agent, or Firm*—Townsend and Townsend and Crew LLP; Gerald T. Gray

(57) ABSTRACT

Probes, and systems and methods for optically scanning a conical volume in front of a probe, for use with an imaging modality, such as Optical Coherence Tomography (OCT). A probe includes an optical fiber having a proximal end and a distal end and defining an axis, with the proximal end of the optical fiber being proximate a light source, and the distal end having a first angled surface. A refractive lens element is positioned proximate the distal end of the optical fiber. The lens element and the fiber end are both configured to separately rotate about the axis so as to image a conical scan volume when light is provided by the source. Reflected light from a sample under investigation is collected by the fiber and analyzed by an imaging system. Such probes may be very compact, e.g., having a diameter 1 mm or less, and are advantageous for use in minimally invasive surgical procedures. A fluid medium can be introduced between two lens elements at the distal end of the probe to switch a mode from side viewing to forward viewing.

17 Claims, 5 Drawing Sheets

U.S. PATENT DOCUMENTS

| | | | |
|---|---|---|---|
| 6,408,112 B1 * | 6/2002 | Bartels .................... 385/16 |
| 6,485,413 B1 | 11/2002 | Boppart et al. |
| 6,626,828 B2 | 9/2003 | Dohi et al. |
| 6,636,664 B2 | 10/2003 | Snyder et al. |
| 6,687,429 B2 * | 2/2004 | Chung .................... 385/19 |
| 6,891,984 B2 * | 5/2005 | Petersen et al. ........... 385/12 |
| 2004/0076390 A1 * | 4/2004 | Yang et al. ............... 385/116 |
| 2004/0247268 A1 * | 12/2004 | Ishihara et al. ........... 385/117 |

* cited by examiner

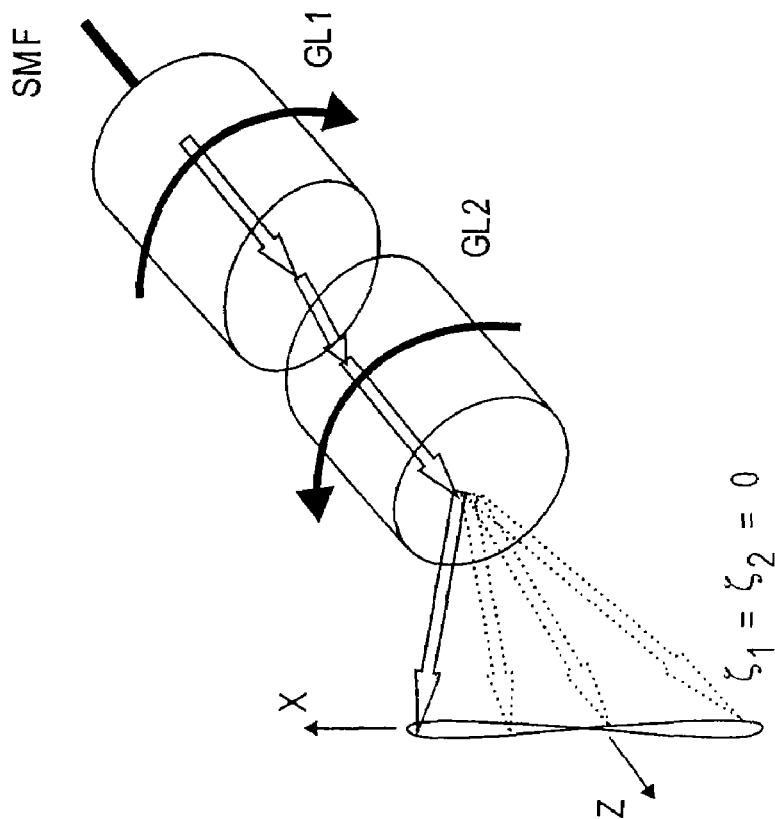
FIG. 6D
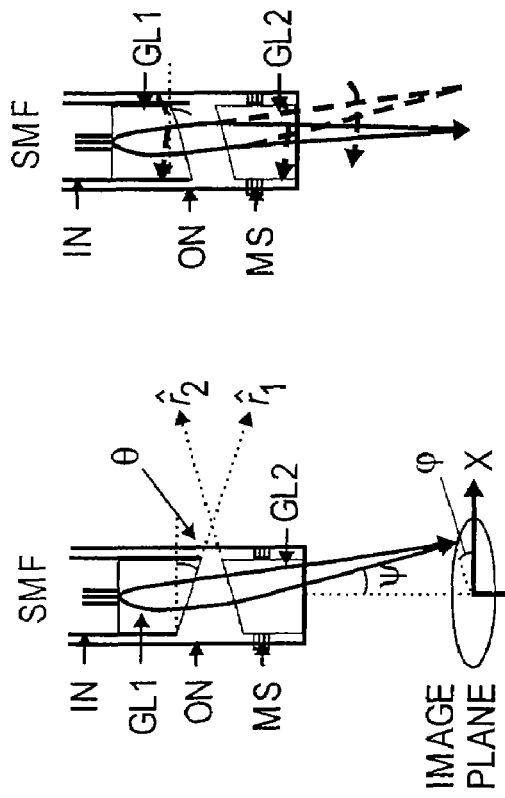
FIG. 6A
FIG. 6B
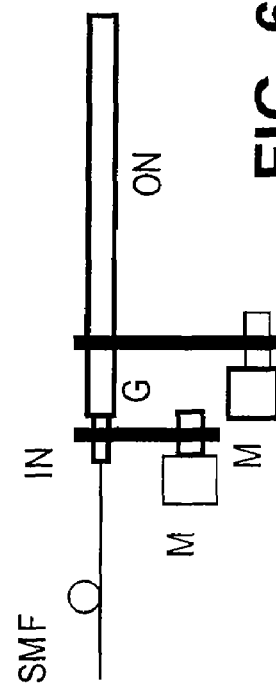
FIG. 6C

PAIRED ANGLED ROTATION SCANNING PROBES AND METHODS OF USE

CROSS-REFERENCES TO RELATED APPLICATIONS

This application is a continuation-in-part of U.S. patent application Ser. No. 11/087,396, filed Mar. 22, 2005 now U.S. 7,261,687, which claims the benefit of U.S. Patent Application No. 60/555,628 filed Mar. 23, 2004, the disclosures of which are incorporated herein by reference in its entirety. This application also claims the benefit of U.S. Provisional Patent Application Nos. 60/770,936, filed Sep. 27, 2005, 60/720,934, filed Sep. 27, 2005, and 60/737,603, filed Nov. 17, 2005, the disclosures of which are hereby incorporated by reference.

STATEMENT AS TO RIGHTS TO INVENTIONS MADE UNDER FEDERALLY SPONSORED RESEARCH OR DEVELOPMENT

The government may have certain rights to the invention based on National Institutes of Health Grant No. 5R21EB004602-02.

BACKGROUND OF THE INVENTION

The present invention relates generally to optical probes and more particularly to optical probes for use with Optical Coherence Tomography (OCT) and other optical imaging modalities.

OCT is a laser based imaging modality that uses near infrared or infrared laser light to non-destructively image subsurface tissue structures. An imaging depth on the order of millimeters (mm), with a spatial resolution of a few micrometers ($\mu m$) is relatively easily achieved using OCT at practical light fluence levels on the order of 100 $\mu W$. OCT is therefore very useful for in vitro and in vivo tissue structure imaging applications such as may be used during minimally invasive surgical procedures. Currently, both side-imaging endoscope systems and forward imaging endoscope systems are known.

The construction of a needle endoscope that is capable of performing forward OCT imaging presents very significant design challenges. Current endoscopes are typically more than 5 mm thick. The thickness of such probes, especially when compared with their en face imaging area, e.g., about 2 mm wide, makes them undesirable as a needle endoscope for image-guided surgical procedures. One major challenge of making a thin endoscope lies with the difficulty of designing a probe beam deflection system that is capable of covering a sufficient scan volume while constraining the probe diameter to be less than about 2 mm to minimize the invasiveness of the probe. A reasonable OCT scan volume for providing sufficient image information would be a conical volume that is about 3 mm in length and about 2 mm in diameter at its maximum circumference.

Therefore it is desirable to provide probes such as forward and side-imaging endoscope needles useful for OCT imaging of a scan volume that overcome the above and other problems.

BRIEF SUMMARY OF THE INVENTION

The present invention provides forward imaging optical endoscope probes useful in imaging applications, and particularly in imaging applications using OCT as the imaging modality. The endoscope probes of the present invention advantageously allow for improved high-resolution imaging of non-transparent tissue structures in the vicinity of the endoscope needle tip.

According to the present invention, a probe includes an optical fiber having a proximal end and a distal end and defining an axis, with the proximal end of the optical fiber being proximate a light source, and the distal end having a first angled surface. A refractive lens element is positioned proximate the distal end of the optical fiber. The lens element and the angled fiber end are both configured to separately rotate about the axis so as to image a conical scan volume when light is provided by the source. Light received from a sample under investigation (e.g., reflected, scattered, excited fluorescence, etc.) is collected by the fiber and analyzed by an imaging system. Such probes may be very compact, e.g., having a diameter 1 mm or less, and are advantageous for use in minimally invasive surgical procedures.

In one aspect, an OCT needle probe is provided that can perform both side imaging and forward imaging. In one aspect, switching between the two scanning modes is done by filling or extracting a fluid between two GRIN lenses, or other lens elements. In one aspect, the end face of a first lens element has an angle that is at, or exceeds, the critical angle for the end face/air interface such that in the side-imaging mode, when no fluid is present between the lenses, light reflects substantially perpendicular to the axis. In a forward-imaging mode, when fluid is introduced, the index of the fluid is sufficient to increase the critical angle of the end-face/fluid interface beyond the lens angle such that light from the source refracts toward the second lens element.

According to one aspect of the present invention, an optical apparatus is provided that typically includes an optical fiber having a proximal end and a distal end and defining an axis, wherein the proximal end of the optical fiber is proximate a light source, and wherein the distal end is proximal a first refractive lens element, that has an end face having a first angle relative to a plane normal to the axis. The apparatus also typically includes a second refractive lens element proximate the first lens element, wherein the second lens element is configured to rotate about the axis, and wherein the first lens element is configured to rotate about the axis separate from the second lens element. The apparatus also typically includes a mechanism for introducing and removing a fluid medium from a region between the first and second lens elements. In typical operation, when in a first mode, with no fluid present in said region, input light from the light source is reflected by the end surface of the first refractive lens element in a direction substantially perpendicular to said axis. In typical operation, when in a second mode, with fluid present in said region, input light from the light source refracts at the end surface of the first refractive element toward the second refractive lens element. In certain aspects, the fluid has an index of refraction of about 1.10 or greater and the first angle is about 38° or greater.

According to yet another aspect of the present invention, a method is provided for imaging a forward scan volume of a tissue sample using a forward scanning probe that typically includes an optical fiber including a proximal end and a distal end and defining an axis, wherein the proximal end of the optical fiber is proximate a light source, and wherein the distal end is proximal a first refractive lens element. The probe further typically includes an imaging end having a second refractive lens element positioned proximate the first lens element, wherein the probe further includes an imaging end having a second refractive lens element positioned proximate to the first lens element and defining a cavity therebetween, wherein the second lens element is configured to rotate about the axis, and wherein the first lens element is configured to rotate about the axis separate from the second lens element. The method typically includes positioning the imaging end of the probe proximal a tissue sample to be imaged, and providing a light beam to the proximal fiber end from the light source. In a forward-imaging mode, the method typically includes introducing a fluid into said cavity, rotating the inner tube at a first rate, and simultaneously rotating the outer tube at a second rate different from the first rate. In a side-imaging mode, the method typically includes removing fluid in the cavity, if present, and rotating the inner tube. In certain aspects, the fluid has an index of refraction of about 1.10 or greater and the first angle is about 38° or greater.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 6 shows a schematic of a PARS-OCT probe according to one embodiment.

FIG. 6(a) shows a configuration with an angle between the two angled surfaces of the GRIN lenses such that the exit (laser) beam is tilted; FIG. 6(b) shows a configuration where the two angled surfaces of the GRIN lenses are parallel and the exit (laser) beam is undeviated; FIG. 6(c) shows a PARS-OCT probe setup including actuation elements; FIG. 6(d) shows a profile of a PARS-OCT B-scan mode.

FIG. 7 illustrates a probe that can be switched between side-imaging and forward-imaging modes according to one embodiment.

FIG. 8 shows various PARS-OCT probe design variations.

DETAILED DESCRIPTION OF THE INVENTION

The present invention provides novel probes, and systems and methods for optically scanning a conical volume in front of a probe, for use with an imaging modality, such as Optical Coherence Tomography (OCT). Other useful imaging modalities for which probes of the present invention are useful include Optical Doppler Tomography (ODT), and Speckle Decorrelation Tomography (SDT).

Figure 1:
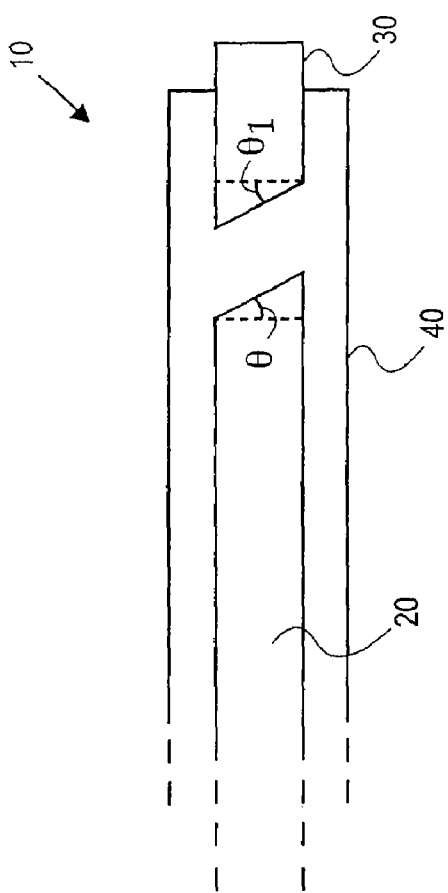
FIG. 1 illustrates a side view of a probe design including a fiber and a lens element according to one embodiment.

A probe 10 according to one embodiment is shown in FIG. 1. As shown, probe 10 includes an optical fiber 20 and a lens element 30 proximal the end of fiber 20. A tube 40 encloses fiber 20. Tube 40 is also coupled to lens element 30 to facilitate rotation of lens element 30 relative to fiber 20. Fiber 20 may itself be rotated separately from tube 40, in one aspect, as will be described in more detail below with reference to FIG. 5.

Figure 2:
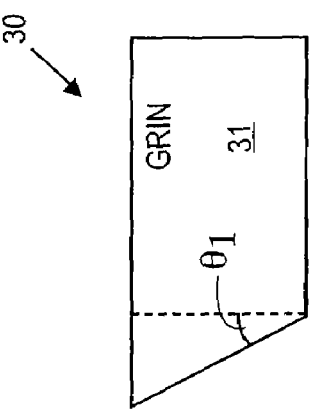
FIG. 2 illustrates a side view of a lens element design according to one embodiment.
Figure 3:
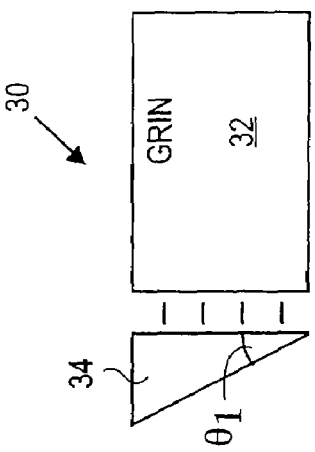
FIG. 3 illustrates another embodiment of a lens element design.

In one aspect, fiber 20 includes a single mode fiber (SMF; although multimode fibers can be used if desired) having an end that is angled cut at an angle of θ as shown in FIG. 1. Input light from a light source (not shown) positioned proximal a distal end of fiber 20 enters fiber 20 and exits at the end of fiber 20 proximal lens element 30. The light exiting from the fiber 20 will be incident on focusing lens element 30. In one aspect, it is preferred that the light source provides collimated light in the infrared (IR) or near-IR wavelength range. Other wavelengths may be used as desired. One example of a useful light source is a laser or a diode laser that emits light in the IR or near-IR wavelength range. FIGS. 2 and 3 show examples of two possible ways the focusing lens element 30 may be constructed.

According to one embodiment, as shown in FIG. 2, lens element 30 includes a (cylindrical) GRIN lens 31 that is cut and polished at one end to have an angle of $\theta_1$. The angle $\theta_1$ is chosen so that when the GRIN lens 31 and the end of fiber 20 are oriented in the manner shown in FIG. 1, the exiting light beam from the GRIN lens 31 is focused in the forward direction. In one aspect, therefore, the angle $\theta_1$ should be substantially the same or similar (e.g., within 1° or 2°) to θ, the angle at the fiber end.

According to another embodiment, as shown in FIG. 3, lens element 30 includes a (cylindrical) GRIN lens 32 and an angled glass wedge element 34 attached to the GRIN lens 32. Wedge element 34 is preferably formed (e.g., cut and polished) from a cylindrical glass element. Wedge element 34 may be glued or otherwise secured to GRIN lens 32. The choice of angle cut presented by the wedge 34 is determined by the same considerations as described above. For example, the angle $\theta_1$ should be substantially the same or similar (e.g., within 1° or 2°) to θ, the angle at the fiber end.

Figure 4:
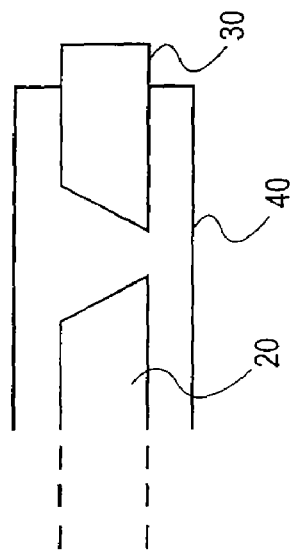
FIG. 4 illustrates an orientation of the elements of FIG. 1 that results in a maximum angle of the forward light beam with respect to the forward axis.

In one aspect, rotation of the GRIN lens element 30 shown in FIG. 2 (or the GRIN-wedge construction shown in FIG. 3) with respect to a fixed fiber orientation will vary the angle of the forward light beam from zero degrees to a certain angle with respect to the forward axis. Zero angle is achieved when the two elements are oriented as shown in FIG. 1. The maximum angle is achieved when the two elements are oriented as shown in FIG. 4. A visualization of the zero angle and maximum angle can be seen in FIGS. 5b and 5a, respectively, which illustrate a slightly different probe configuration. The continuous rotation of the lens element 30 between those two orientations will complete a span of the angle between the zero angle and maximum angle values. Therefore, in one aspect, rotation of both elements will allow for a conical scan volume to be imaged. For example, rotating the fiber 20 at one rate and the GRIN lens 30 of FIG. 2 (or GRIN-wedge construction of FIG. 3) at a different rate allows for a forward conical scan volume to be taken.

The focal length of the lens element 30 and the distance from the tip of fiber 20 is preferably selected so that the output light forms a focus at an appropriate desired distance in the foreground. For example, in an OCT imaging system, the focal point can be chosen to be at half the penetration depth of the OCT imaging capability. A useful focus length for many applications is about 2.0 mm, however, it should be understood that a focal length of between about 0.1 mm and about 10 mm or more can be implemented.

FIG. 5 illustrates a probe 110, and a probe scan system, according to an embodiment of the present invention. In the embodiment shown, optical probe 110 includes a pair of GRIN lenses and a pair of cylindrical glass elements that are cut at an appropriate angle θ. As shown, probe 110 includes an optical fiber 120 and a fiber lens element 125 proximal the end of fiber 120. A first tube 140 ("inner tube") encloses fiber 120. Inner tube 140 is also coupled to fiber lens element 125 to facilitate rotation of lens element 125. A second rotatable tube 150 ("outer tube") encloses tube 140 and refractive lens element 130 to facilitate rotation of lens element 130 relative to fiber lens element 125. Input light from a light source (not shown) at a distal end of fiber 120 enters fiber 120 and exits the fiber end internal to inner tube 140 as shown. In one aspect, the optical fiber 120 is fixed at the focal point of fiber lens element 125 within the inner tube. In preferred aspects, lens element 125 includes a GRIN lens. The GRIN lens may be cut at an angle or it may be coupled with an angled wedge element (e.g., similar to wedge 34 discussed above with reference to FIG. 3) as shown. In this case, the light output is collimated by the GRIN lens and angularly displaced by the angled glass wedge element. The tilted beam is brought to a focus by lens element 130, which in one aspect as shown includes a second glass wedge element and GRIN lens pair, and which is attached to the outer tube.

Figure 5A:
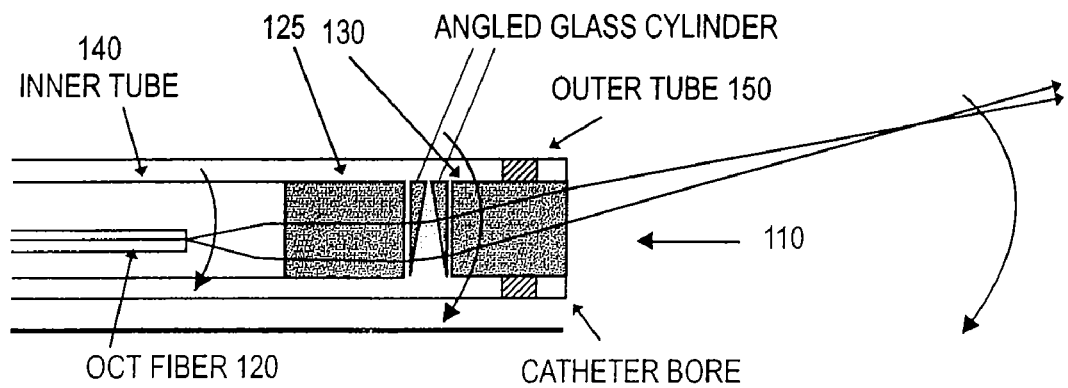
FIG. 5a illustrates a side view of a probe design according to another embodiment of the present invention.

The rotation of lens element 130 with respect to fiber lens element 125 will change the angle of the forward light beam with respect to the forward axis. For example, FIG. 5a shows the orientations that provide a maximum angle, and FIG. 5b show the orientations that provide a zero angle.

The operating principle of the paired angled rotation scanning OCT (PARS-OCT) probe embodiments will now be described with reference to FIG. 6. As shown in FIGS. 6(*a*) and 6(*b*), the PARS-OCT probe channels the input OCT probe light from a single mode fiber (SMF) through the first GRIN lens. The light beam exits from the other face of the GRIN lens which is cut at an angle θ. The beam then enters the second GRIN lens (or a glass cylinder) through a similarly angle-cut face of the GRIN lens. The beam then exits the second GRIN lens and focuses at a point ahead of the probe. The exact focal point is determined by the pitch of the two GRIN lenses. For completeness, the orientations of the two GRIN lenses by angle $\zeta_1$ and $\zeta_2$ are defined as the angles between the projections of vectors $\hat{r}_1$, and $\hat{r}_2$, respectively, in the image plane and the x-axis as shown in FIG. 6(*a*). The direction of the output light beam is defined by its polar angle ψ that it makes with the z-axis and its azimuthal angle φ; an angle of ψ=0 implies that the exit beam propagates along the z-axis. In the proximal end, the rotations of the needles that contain the GRIN lenses or glass rod are driven by two motors, as shown in FIG. 6(*c*).

A fan sweep of the output beam in xz-plane as shown vertical in FIG. 6(*d*) can be performed by rotating the two GRIN lenses in opposite directions at the same angular speed from the starting position where the two GRIN lenses are oriented such that $\zeta_1=\zeta_2=0$. This scan pattern can be understood by taking a closer look at the output beam orientation when $\zeta_1=\zeta_2=0$ as shown in FIG. 6(*a*). In this case, the exit beam from the first GRIN lens is deflected in the xz-plane such that φ=0. Notice that the second GRIN lens with $\zeta_2=0$ further bends the beam (keeping φ=0), which is shown as downward deflection in FIG. 6(*d*). When the two GRIN lenses begin rotating by an equal and opposite amount ($\zeta_1=-\zeta_2>0$), the downward deflection of the exit beam from the first GRIN lens will lessen and the beam will lean to the left if the probe is viewed head on. The shifting of the beam to the left will be compensated by the second GRIN lens which conveys an equal but opposite shift to the beam; the downward deflection contribution of the beam by the second GRIN lens will lessen as well. The net effect is a smaller downward deflection of the beam and little or no horizontal shifting. Continued rotations of the GRIN lenses will eventually result in the GRIN lenses orientation of $\zeta_1=90°$ and $\zeta_2=-90°$. In this configuration (see FIG. 6(*b*)), the two GRIN lenses compensate for each other's deflection of the beam and result in an output beam that is undeflected. Further rotation of the GRIN lenses will then deflect the beam upwards. A complete 180° rotation of the GRIN lens will therefore result in a vertical sweep of the output beam from its down position to its up position—a fan sweep or an effective OCT B-scan.

Figure 5B:
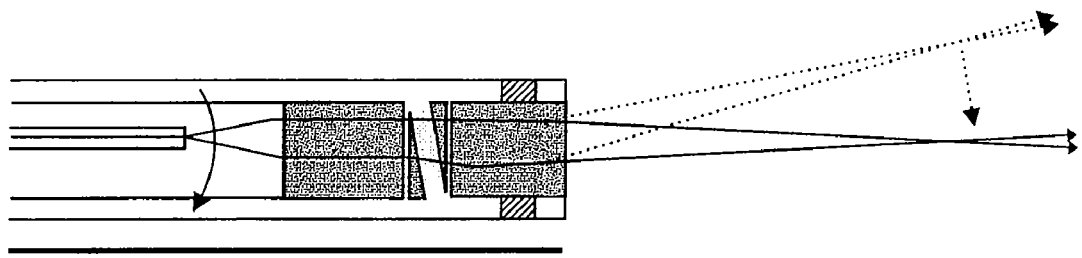
FIG. 5b illustrates an orientation of the elements of FIG. 5a that results in a zero angle of the forward light beam with respect to the forward axis.

In mathematical terms, if the angular difference between the orientation of the first and second angled surfaces is given by Δφ (Δφ=0 when the cylinders are oriented as shown in FIG. 5*b* and FIG. 6*b*), the angle made by the output beam to the forward axis is approximately given by: $\psi \approx \theta \sqrt{(n-1)^2(1-\cos(\Delta\phi)^2)+\sin(\Delta\phi)^2}$ (6)

where n is the refractive index of the cylinders. By rotating fiber lens element 125 with respect to lens element 130, the angle ψ made by the output beam relative to the forward axis can be changed from 0 to 2(n−1) rads. Rotating both lens elements synchronously results in a scan of the output beam in a complete circular cone. If the focal point of the output is 2 mm from the probe tip and it is desirable to cover a scan area 2 mm in diameter at that distance, the angular cut, θ, should be about 0.19 rads (about 11°). Given the smallness of the angle, in one aspect, the design is further simplified by cutting the GRIN lenses with the given angular tilt, eliminating the need for glass wedge elements.

Figure 5C:
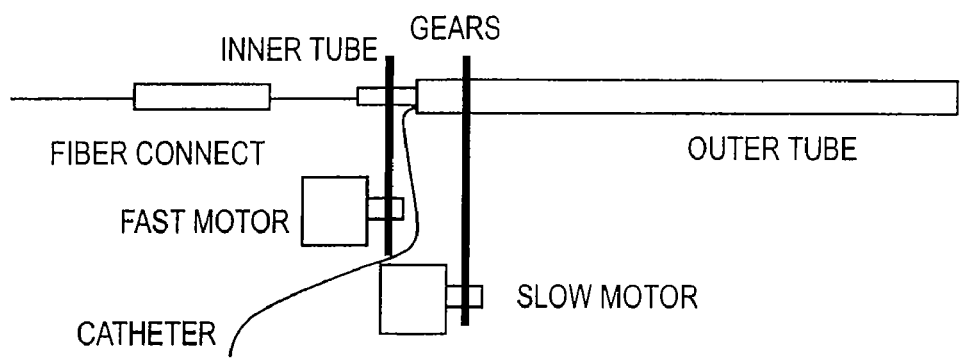
FIG. 5c illustrates a rotation actuation system according to one embodiment.

In one embodiment, the outer and inner tubes (e.g., holding lens element 130 and fiber 120, respectively) are preferably mounted to two different motors via gears as shown in FIG. 5*c*. In the embodiment of FIG. 1, tube 40 and fiber 20 may similarly be coupled to different motors. In both cases, the complete rotation of the refractive lens element and the fiber end with respect to a reference plane will complete a conical sweep. Therefore, the combination of these two motions will create a scan volume equal to a solid cone with a maximum angle from the forward axis given by the considerations described above. Each motor preferable provides one or multiple rotational speeds in the range of a fraction of 1 HZ to about 1 KHz or more. Also, each motor may rotate the coupled elements in the same or opposite direction as the other motor. Further, the fiber 120 need not rotate with the fiber lens element 125; that is inner tube may rotate without rotation of fiber 120. It should also be appreciated that a single motor may be used to rotate both the inner and outer tubes. In this case, a ratchet and pawl type mechanism coupling the motor to both tubes may be used to rotate the tubes at different rotational speeds.

Examples of a similar rotation actuation system and a fiber connection to an OCT imaging system for a side scanning probe is shown in "Scanning single-mode fiber optic catheter-endoscope for optical coherence tomography", Optics Letters, V21, μg. 543 (1996), which is hereby incorporated by reference. Moreover, it should be appreciated that the distance between the GRIN lenses (or other refraction elements) may be adjusted either automatically or manually.

By using OCT imaging to create depth resolved imaging along each light beam path orientation, a three dimensional image of the structure in front of the imaging needle (probe) can be constructed. For example, an imaging Fourier Domain OCT (FDOCT) engine can be used with the probes of the present invention to acquire tomographic images of the forward scan volume. Given the large forward scan volumes possible (e.g., about 3-4 mm forward and an area of diameter 4 mm at the 4 mm forward distance point), a needle endoscope according to embodiments of the present invention provides unprecedented forward imaging capability. For example, by rotating the inner tube at 100 Hz and the outer tube at 1 Hz, a 3 dimensional image with a total of $10^8$ voxel per second can be generated with an OCT imaging system that is capable of acquiring 100 kHz rate A-scans with 1,000 pixels each.

There are many major advantages associated with this probe design. For example, by attaching the GRIN lenses to separate concentric needle shafts, actuation of the GRIN lenses rotations can be done by simply turning the needle shafts. This can be done with actuators that are located far from the probe tip. Additionally, by minimizing the distance between the two GRIN lenses, the probe optical design can be optimized and the probe beam enabled to almost completely fill the output face of the second GRIN lens. This effectively increases the projection and collection numerical aperture of the probe, and enables the probe to approach its theoretical numerical aperture maximum. In other reported forward-imaging OCT probe designs, the achievement of such a goal is hindered by the scan mechanism. Moreover, this probe design allows for obtaining a complete volumetric scan of the forward region. There are several ways to acquire such a volumetric scan. One way is to acquire a series of B-scans through the scan scheme described above and incrementally change the starting relative GRIN lenses' orientation between each scan. Additionally, the innovative and yet elegantly simple design enables very compact probes to be built, e.g., probes of diameter 1 mm or less (e.g., 500 microns or less). Such devices provide a dramatic improvement over existing endoscopic imaging technology. The compact size and forward tomographic imaging capability of the probes of the present invention make image guidance of minimally invasive surgical procedure possible.

Figure 7A:
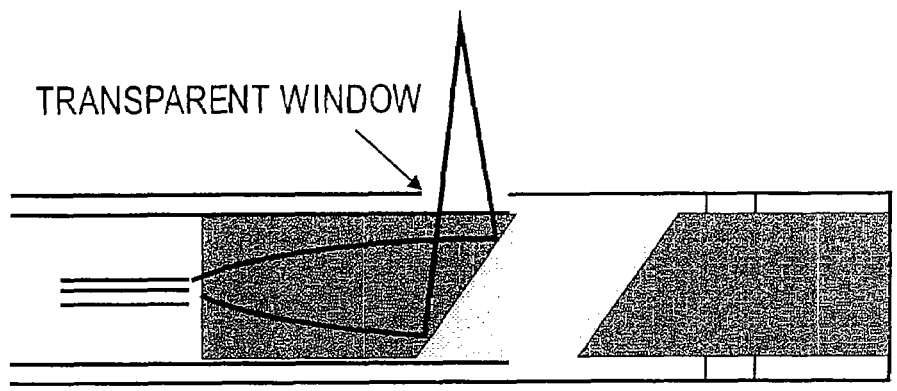
FIG. 7(a) shows a side-imaging scanning mode achieved by using total internal reflection.

FIG. 7 illustrates a probe that can be switched between side-imaging and forward-imaging modes according to one embodiment. In one aspect, the angle cut on the first GRIN lens exceeds the critical angle for the glass-air interface. Given that the refractive index of the GRIN lens is typically 1.6, this indicates that the cut angle should be at least 38.7°. With this choice, the output beam necessarily reflects from the angled surface and exits the probe at an angle that is approximately normal to the probe axis. If the angle cut chosen for the GRIN lens is 45°, the output beam should be exactly normal to the probe axis. By making sure that the needle shafts are transparent along the output path (by either using transparent needle shafts or building windows into the shafts), the focused output beam can be used as a side imaging probe beam. Rotation of the inner needle shaft in tandem with the outer shaft results in a cross-sectional OCT scan. FIG. 7(a) demonstrates a side-imaging probe configuration.

Figure 7B:
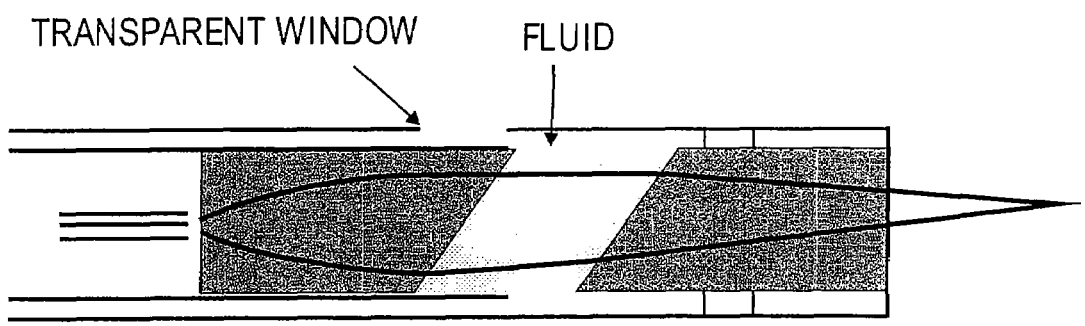
FIG. 7(b) shows a fluid introduced between the two GRIN lenses to change the direction of the light and achieve forward-imaging scanning.
Figure 8A:
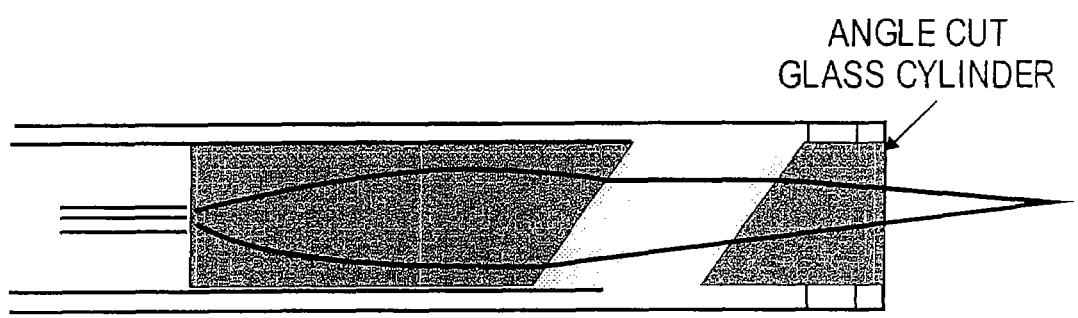
FIG. 8(a) shows a configuration including a glass cylinder in the place of a GRIN lens.
Figure 8B:
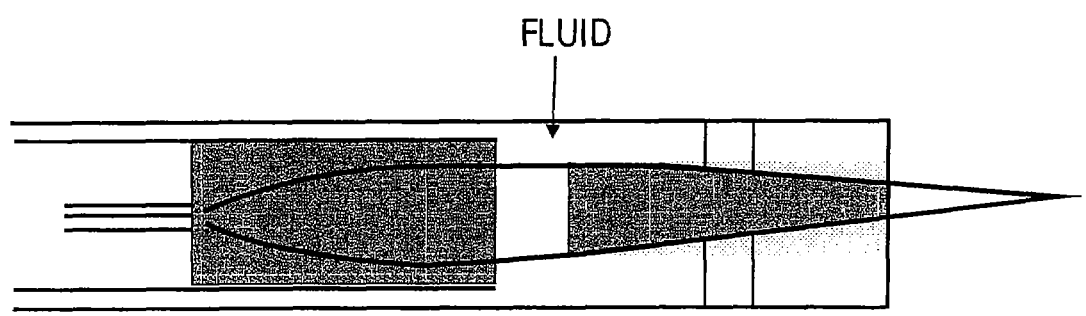
FIG. 8(b) shows a fluid medium inserted between the two GRIN lenses.

According to one embodiment, the output direction of the beam is controllably changed by introducing a fluid between the GRIN lens and the glass cylinder (or second GRIN lens) so as to change the critical angle for the GRIN lens output interface. For example, assuming an angle cut of 45°, a fluid with refractive index greater than 1.13 is sufficient for the beam to exit the angled surface, although fluid having a larger index may be better for efficiency considerations. The output beam is then transmitted to the glass cylinder which has a similar angle cut. This probe may now function as a forward-imaging probe, as shown in FIG. 7(b). In certain aspects, fluid is introduced and removed from the cavity between the refraction elements via a fluid port coupled with a fluid reservoir by a pump or other actuation mechanism. A fluid channel can be incorporated into the probe to provide a passage for the fluid.

In addition to use with Optical Coherence Tomography, the probes of the various embodiments may be used for channeling a sufficiently high light dosage for welding, ablation, or cutting. The steering mechanism in the probe may also be used to steer the output beam. For example, this approach may be used to 'drill' a hole through the medium for the progressive insertion of the needle. Suitable medium candidates include tissue, membranes and any other medium that is absorptive in the optical, infrared or UV range. The light dosage required for ablation, welding and cutting differs greatly from medium types and light source types. As a guide, muscle tissue cutting requires at least 10 mW of femtosecond pulse light (at 100 MHz) repetition rate focused onto a spot of diameter 10 microns. The applications for this method include: 1) Blood vessel plaque removal, which can be done with a forwarding or side-imaging probe, 2) Surgical removal of diseased tissue via needle probes, and 3) Brain surgery ablation of tissues.

The probes of the various embodiments may also be used with other imaging techniques such as fluorescence, 2 photon fluorescence, Raman, Coherent Anti-Stokes Raman Spectroscopy, and other imaging modalities.

Design Variations

In certain aspects, an angle cut glass cylinder is used in place of one or both of the lens elements (e.g., elements 125 and 130). By extending the first GRIN lens' pitch to beyond ¼ pitch, a converging output beam can be obtained from the lens. If properly designed, the use of the second GRIN lens to focus the output beam is not required. A second angled surface is still required to pivot and steer the beam; this functionality can be addressed with an angled cylindrical lens.

According to certain aspects, a graded index fiber, or photonic crystal fiber is used in place of the GRIN lens elements.

According to certain aspects, insertion of fluid within the space between the two optical elements is useful to correct chromatic aberration and/or allow dynamic focusing. The concept of filling the space between the two GRIN lenses with a fluid is advantageous in reducing the second type of chromatic aberration artifacts. For example, if the dispersion property of the fluid matches with those of the GRIN lenses (and the average refractive of the fluid is still different from those of the GRIN lenses), each wavelength components of the light beam will be bent by the same amount during passage through and out of the GRIN lenses and fluid interface. The second type of chromatic aberration artifacts can thus be suppressed. Further, insertion of a fluid can be used to alter the focal depth of the output beam from the PARS-OCT probe. This can be particularly useful in works that involves different tissue types where the penetration depth may vary during the needle surgical procedure. The change in focal depth can simply be brought about by changing the net refractive index of the fluid medium. The respective effort to correct chromatic aberration and enable depth of focus change do not conflict. One involves selecting the right refractive dispersion for the fluid medium, the other involves changing the net refractive index.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, rather than having a flat end face, a GRIN lens may be angled cut and a wedge element may be attached thereto and cut so as to provide the desired angled surface, e.g., $\theta$ or $\theta_1$. Additionally, the tubes holding the lens elements and fibers may comprise a flexible or rigid material. Therefore, the scope of the appended claims should be accorded the broadest interpretation so as to encompass all such modifications and similar arrangements.

What is claimed is:

1. An optical apparatus, comprising:
   an optical fiber including a proximal end and a distal end and defining an axis, wherein the proximal end of the optical fiber is proximate to a light source, and wherein the distal end is proximal a first refractive lens element, wherein the first lens element includes an end surface that is angled cut at a first angle relative to a plane normal to said axis; and
   a second refractive lens element proximate to the first lens element, wherein the second lens element is configured to rotate about said axis, and wherein the first lens element is configured to rotate about said axis separate from the second lens element; and
   a mechanism for introducing and removing a fluid medium from a region between the first and second lens elements,
   wherein in a first mode, with no fluid present in said region, input light from the light source is reflected by the end surface of the first refractive lens element in a direction substantially perpendicular to said axis, and
   wherein in a second mode, with fluid present in said region, input light from the light source refracts at the end surface of the first refractive element toward the second refractive lens element.

2. The apparatus of claim 1, wherein the first lens element includes a GRIN lens that is angled cut at the first angle relative to a plane normal to said axis.

3. The apparatus of claim 1, wherein the second lens element includes a GRIN lens that is angled cut at a second angle relative to the plane normal to said axis, said second angle being substantially the same as the first angle.

4. The apparatus of claim 1, wherein the second lens element includes a glass cylinder that is angled cut at a second angle relative to the plane normal to said axis, said second angle being substantially the same as the first angle.

5. The apparatus of claim 1, wherein the first lens element includes a GRIN lens and an optical wedge element attached thereto, said wedge element providing an end face at a first angle relative to a plane normal to said axis.

6. The apparatus of claim 1, wherein the second lens element includes a second GRIN lens and a second optical wedge element attached thereto, said second wedge element providing an end face at a second angle relative to a plane normal to said axis, said second angle being substantially the same as the first angle.

7. The apparatus of claim 1, further comprising a first motor coupled with the fiber, and a second motor coupled with the second lens element, wherein the first motor is configured to rotate the first lens element about said axis, and wherein the second motor is configured to rotate the second lens element about said axis in a different or same rotational direction as the first lens element.

8. The apparatus of claim 1, wherein one or both of the first lens element and the second lens element includes one of a GRIN lens, a graded index fiber or a photonic crystal fiber.

9. The apparatus of claim 1, wherein the fluid has an index of refraction of approximately 1.10 or greater.

10. The apparatus of claim 1, wherein the first angle is approximately 38° or greater.

11. A method of imaging a tissue sample using a scanning probe that can be operated in a forward-imaging mode and a side-imaging mode, wherein the probe includes an optical fiber including a proximal end and a distal end and defining an axis, wherein the proximal end of the optical fiber is proximate to a light source, and wherein the distal end is proximal a first refractive lens element, wherein the first lens element includes an end surface that is angled cut at a first angle relative to a plane normal to said axis, wherein the probe further includes an imaging end having a second refractive lens element positioned proximate to the first lens element and defining a cavity therebetween, wherein the second lens element is configured to rotate about the axis, and wherein the first lens element is configured to rotate about the axis separate from the second lens element, the method comprising:
   positioning the imaging end of the probe proximal a tissue sample to be imaged;
   providing a light beam to the proximal fiber end from the light source; and
   in a forward-imaging mode:
      introducing a fluid into said cavity;
      rotating the inner tube at a first rate; and
      simultaneously rotating the outer tube at a second rate different from the first rate; and
   in a side-imaging mode:
      removing fluid in the cavity, if present, and rotating the inner tube.

12. The method of claim 11, wherein light reflected by the tissue sample is collected in the fiber, the method further comprising capturing the reflected light from the tissue sample in the fiber using one of an optical coherence tomography imaging system, a fluorescence imaging system a 2-photon fluorescence imaging system, a Raman imaging system, or a coherent anti-Stokes Raman spectroscopy system.

13. The method of claim 11, wherein the light beam has a wavelength in one of the IR or near-IR wavelength spectrum.

14. The method of claim 11, wherein each of the inner tube and outer tube is rotated at between approximately 1 Hz and approximately 1 kHz.

15. The method of claim 14, wherein the inner tube is rotated at approximately 100 Hz and wherein the outer tube is rotated at approximately 1 Hz.

16. The method of claim 14, wherein the first angle is at or exceeds the critical angle for an end face-air interface when no fluid is present in the cavity.

17. The method of claim 11, for use in one of a blood vessel plaque removal procedure, a surgical removal of tissue procedure or a brain surgery ablation of tissue procedure.

* * * * *